United States Patent [19]
Siekmeyer et al.

[11] Patent Number: 5,846,196
[45] Date of Patent: Dec. 8, 1998

[54] INTRAVASCULAR MULTIELECTRODE CARDIAC MAPPING PROBE

[75] Inventors: Gerd Siekmeyer, Brussels, Belgium; Wilhelmus Petrus Martinus Maria van Erp, Leek, Netherlands

[73] Assignee: Cordis Europa N.V., Netherlands

[21] Appl. No.: 764,368

[22] Filed: Dec. 12, 1996

[30] Foreign Application Priority Data

Dec. 13, 1995 [NL] Netherlands ............................ 1001890

[51] Int. Cl.$^6$ .................................................. A61B 5/042
[52] U.S. Cl. ........................... 600/374; 600/393; 606/41; 607/122
[58] Field of Search .................................. 600/374, 393; 606/41; 607/122, 129, 138, 148

[56] References Cited

U.S. PATENT DOCUMENTS

| | | |
|---|---|---|
| 3,326,207 | 6/1967 | Egan . |
| 3,825,015 | 7/1974 | Berkovits . |
| 3,903,897 | 9/1975 | Woollons et al. . |
| 3,995,623 | 12/1976 | Blake et al. . |
| 4,172,451 | 10/1979 | Kline . |
| 4,425,908 | 1/1984 | Simon . |
| 4,432,369 | 2/1984 | Halvorsen . |
| 4,628,937 | 12/1986 | Hess et al. ............................. 607/129 |
| 4,976,711 | 12/1990 | Parins et al. . |
| 5,010,895 | 4/1991 | Maurer et al. .......................... 607/138 |
| 5,255,679 | 10/1993 | Imran . |
| 5,391,200 | 2/1995 | KenKnight et al. ..................... 607/129 |

FOREIGN PATENT DOCUMENTS

| | | |
|---|---|---|
| 0 682 911 A1 | 11/1995 | European Pat. Off. . |
| WO 94/07411 | 4/1994 | WIPO . |
| WO 94/21165 | 9/1994 | WIPO . |

*Primary Examiner*—Le Cohen

[57] ABSTRACT

An intraventricular multielectrode cardiac mapping probe having an electrode array assembly which is initially stored within the distal lumen of a delivery catheter and after placement of the tip of the catheter at a target location within the heart the electrode array may be moved out of its retracted position to expand into a generally planar configuration to position electrodes for mapping of the heart chamber.

8 Claims, 5 Drawing Sheets

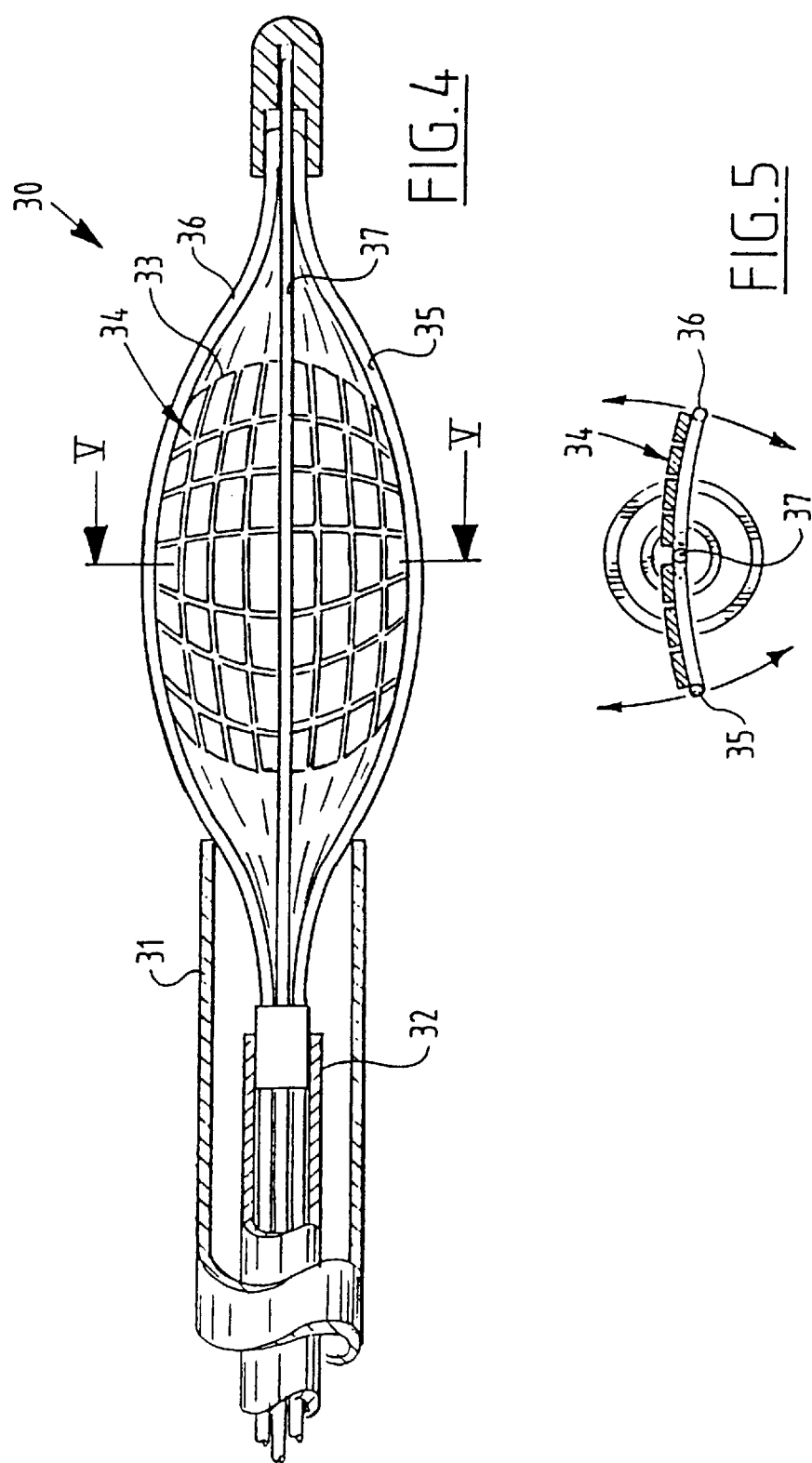

INTRAVASCULAR MULTIELECTRODE CARDIAC MAPPING PROBE

FIELD OF THE INVENTION

The present invention relates to an intravascular multi-electrode cardiac mapping probe for endocardial mapping of a heart chamber.

BACKGROUND OF THE INVENTION

In the procedure of cardiac mapping, electrical potentials are recorded directly from the heart and are depicted as a function of time in an integrated manner. Electrodes are utilized for recording electrical potentials at different positions on the wall surface of a heart chamber, such as the endocardial wall of a ventricle, so that several important electrophysiological variables may be identified from the cardiac recordings. Such variables include local activation times, wave-form analysis, and voltage potential distribution during polarization and repolarization. Cardiac mapping is very important in locating abnormal foci in the heart. Mapping probes may even be utilized to destroy such abnormal foci.

Various techniques of cardiac mapping are disclosed in numerous articles written about cardiac mapping and one very informative article concerning cardiac mapping is entitled, "Techniques of Intraoperative Electrophysiologic Mapping" by John J. Gallagher, et al. which appeared in the January, 1982 issue of "The American Journal of Cardiology," volume 49, pages 221–241.

The medical procedure of cardiac mapping may be performed in an epicardial manner, that is to say, on the exterior wall surface of the heart, or in an endocardial manner, that is within an interior chamber wall or endocardial wall of the heart.

Epicardial mapping often requires a difficult and risky surgical procedure wherein an incision is made through the chest wall. With endocardial mapping, a sensing probe (or electrode) may be passed through a blood vessel and then positioned within the heart chamber at different positions on the wall of the heart chamber in order to conduct a mapping study without the need for an incision through the chest wall.

As may be appreciated that heart mapping can become very involved and risky, and accordingly, it is desirable to provide an endocardial procedure that does not require cutting through the chest wall and through the heart wall while still being able to make endocardial measurements of different potentials on an interior heart chamber wall for creating a potential distribution map. Endocardial mapping is preferred since epicardial mapping can be a very traumatic procedure.

For these reasons, limited invasive endocardial mapping is the preferred procedure for carrying out such mapping. Generally, this procedure utilizes multiple electrodes arranged along a single axis on a single lead in order to provide mapping of the heart wall.

Various devices have been proposed which have multiple electrodes and which can be inserted through a vein or other passageway into a chamber of the heart for mapping voltage potentials within the chamber. Examples of these previous mapping probes are disclosed in the following United States patents:

The United States patent to Egan U.S. Pat. No. 3,326,207, discloses an electrocardiac instrument for testing unborn infants, which instrument includes a balloon on which electrodes are positioned and which can be inserted into the uterus and positioned adjacent a fetus for recording various potentials once the balloon is inflated.

The United States patent to Berkovits, U.S. Pat. No. 3,825,015, discloses a single catheter for atrial and/or ventricular stimulation where the distal end portion of the catheter has a number of ring electrodes mounted thereon which can be used for sensing potentials within a heart chamber such as in the atrium or in the ventricle.

The United States patent to Woollons, et al., U.S. Pat. No. 3,903,897, discloses a cardiac pace maker having several ventricular poles or electrodes at a distal end of the pacing lead and several atrial poles spaced a short distance behind the ventricular poles. The atrial poles are, of course, utilized for sensing potentials within the atrium.

The United States patent to Blake, et al., U.S. Pat. No. 3,995,623, discloses a multipurpose flow directed catheter which has a number of ring electrodes thereon for sensing various potentials within a ventricle and within an atrium.

The United States patent to Kline, U.S. Pat. No. 4,172,451, discloses an intracardiac electrode and a method for manufacturing such a device. The electrode comprises an outer flexible tube containing a plurality of wire leads which extend to perforations in the distal end of a tube forming part of the electrode. The wire lead ends form electrodes which can be utilized for sensing potentials within a heart chamber and particularly for receiving and transmitting electrical impulses from different points on a heart wall to a recording and/or information storage unit for direct observation or subsequent analysis.

Except for the balloon structure shown in the patent to Egan, et al., all of these patents disclosed elongate, mapping probes having distal end portions which have electrodes thereon, and do not provide any form of a probe which can be manipulated from a very small folded position to an expanded position whereby the electrodes form a generally planner surface for measuring various potentials within a heart chamber as provided in the cardiac mapping probe of the present invention.

It has been known in various related medical arts to use assemblies of expandable wires for clearing a blood clot which expandable wires are inserted into a vein or artery in a generally straight configuration and then are caused to expand outwardly to engage the side walls of a vein. Such blood filter assemblies are disclosed in U.S. Pat. No. 4,425,908.

Also it has been proposed to provide an electrode magnetic sensor having three electrodes positioned within an elliptical frame which may be inserted into a vein. A generator of a magnetic field is then utilized for measuring signals from the electrodes with this sensor, such signals being indicative of a biological condition such as fluid flow in a vein or artery, the diameter of a blood vessel, etcetera. Such a device is shown in U.S. Pat. No. 4,432,369.

SUMMARY OF THE INVENTION

As will be described in greater detail hereinafter, the intravascular multielectrode cardiac mapping probe of the present invention differs from the various devices disclosed and described in the patents referred to above by providing a catheter having a lumen which extends for the length of the catheter, an elongate inner tubing is slidably received and movable within the lumen of the catheter, a plurality of elongate insulated conductor assemblies are mounted within the lumen of the elongate inner tubing, and an electrical array assembly including a flexible electrode carrier having a plurality of spaced-apart electrodes which are mounted on the carrier. Each of the electrodes is in electrical continuity, or electrical connection, with one of the conductor assemblies. The electrode carrier is preformed into a generally planner configuration, or other desirable preformed configuration, but is initially in a folded or rolled configuration and is positioned within the lumen of the catheter at the most distal end of the catheter. The electrode carrier exhibits the characteristic that upon being released, it returns to its original preformed configuration so that when the distal end of the catheter is placed in a desired position within the heart chamber, the inner tubing may be slidably moved toward the distal end of the catheter to thereby cause the electrode array assembly to move out of the distal end of the catheter. When the electrode carrier is moved out of the catheter lumen the carrier unfolds or unrolls to thereby expand from its retracted position within the lumen to its predetermined configuration or shape outside of the catheter to permit the measurement of electrical potential within the heart chamber.

BRIEF DESCRIPTION OF THE DRAWINGS

FIG. 4 is a perspective view, with portions broken away, which shows another embodiment of the present invention in which the electrode array assembly is folded prior to insertion into the catheter.

FIG. 5 is a cross-sectional view, taken along the line V—V of FIG. 4.

DESCRIPTION OF THE PREFERRED EMBODIMENTS

Figure 1:
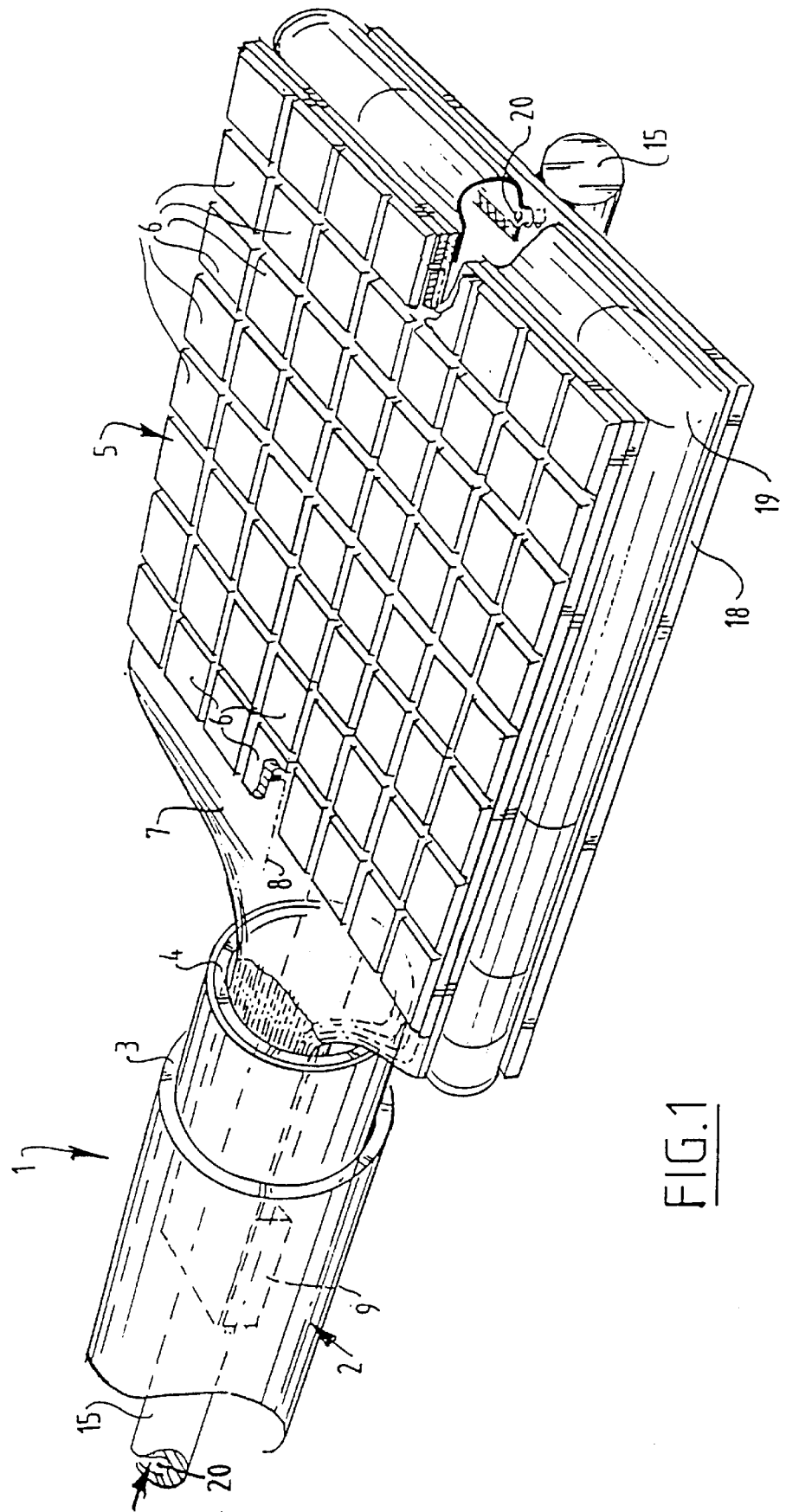
FIG. 1 is a perspective view, with portions broken away, of one embodiment of the intravascular multielectrode cardiac mapping probe of the present invention.

Referring now to FIG. 1, there is illustrated a perspective view of the intraventricular multielectrode cardiac mapping probe 1 constructed in accordance with the teachings of the present invention. As is illustrated, the multielectrode catheter 1 includes an outer cylindrical body 3 having a lumen which extends for the length of the cylindrical body 3. An elongate inner tubing 4 is placed within the lumen of the outer cylindrical body and is slidable or movable in a longitudinal direction.

The elongate inner tubing 4 is made up of a core 12 which has been formed by a helically coiled steel wire, with a rectangular cross section, and is surrounded by a closely fitting outer sheath 11. By employing this construction, the thickness of the wall of the inner tubing 4 can be kept to a minimum so that the overall outside diameter of the catheter 1 can remain as small as possible.

An electrode array 5 takes the form of a cylindrical bar support 15 which has been fixed inside the end of the inner tubing 4, for instance, by means of adhesive 16. As is illustrated, a plate-like electrode carrier 18 has been mounted on the cylindrical bar 15, for supporting the multiple electrodes. A flexible bag 19, which can be filled with a fluid through a channel 20, is mounted on the electrode carrier 18. Finally, and an array of electrode elements 5, has been arranged on top of the flexible support bag 19.

In this embodiment, the electrode array 5 is rectangular in shape and is made up of a plurality of electrodes 6. The electrodes 6 are preferably constructed in the form of printed wiring on a foil substrate 7, as a result the electrode array 5, is very pliable and flexible in use.

Conductors are formed in the foil substrate 7 and have been arranged in the form of printed circuit wiring. The conductors are connected with the electrodes 6 through small passageways in the foil 7. For each electrode 6, a single conductor runs along the back of the foil substrate 7 to a multiplexer 9, which has been mounted on the distal section of the foil 7. The distal end of the foil section 7 is in turn attached to the elongate inner tubing 4.

One of the conductive lines which runs from a single electrode 6 to the multiplexer 9 has been illustrated schematically and is indicated with the reference numeral 8. Signals from the multiplexer 9 are transmitted through conductive wires to proximal connectors of the catheter 1 to thereby permit transmission of the multiplexed signals from the multiplexer 9 to the proximal connectors of the multi-electrode catheter.

In the device illustrated in FIG. 1, the catheter 1 may be used to map electrical activity in the inner wall of the heart of the patient. Particularly, in the case of tachyarrhythmias, it is desirable to map pathways of undesirable electrical activities. To this end, the electrodes 6 of the electrode array 5 are maneuvered against the wall of the heart. Because of the flexibility and compressibility of the support bag 9, filled with a fluid, the electrodes 6 are urged to make proper contact with the surface of the wall. After the mapping of the heart has taken place, an ablation treatment may be carried out in order to interrupt undesirable pathways. By way of the signal lines and the electrodes 6, it is possible to ablate the area of the heart in the region where undesirable foci are located. In this way, the undesired pathways may be interrupted very selectively and at exactly the right location.

After the treatment process, the electrode array may then by folded or rolled up and again drawn into the catheter body for removal from the body of the patient. In one embodiment of the present invention, the carrier 18 of the electrode array 6 may be formed of a memory material such as nitinol. The unfolded state of the carrier 18, that is to say the state in which it forms a more planar or flat sheet, is the relatively relaxed state of the memory metal at a raised temperature. The folded state is the relatively relaxed state at body temperature in order to bring the carrier 18 from the folded state into the unfolded state. Heating means may be arranged on the catheter 18 and may be activated through signal lines which extend to the proximal end of the catheter. When electrical current is turned on, the carrier 18 is heated to above the transition temperature, as a result of which the relatively relaxed unfolded state, as illustrated in FIG. 1, is created. The transition temperature may for instance be designed to occur at approximately 45 degrees centigrade.

Figure 2:
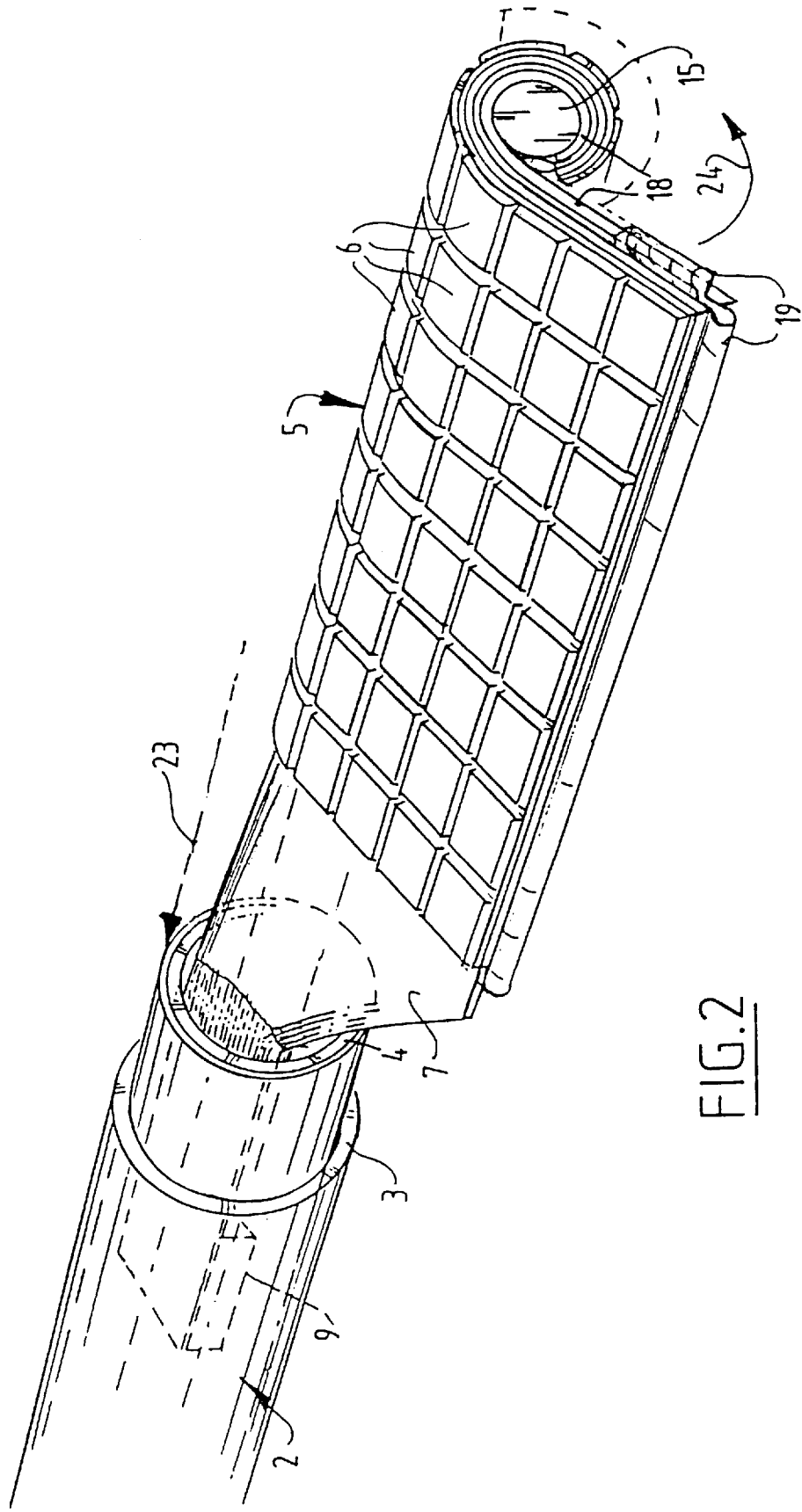
FIG. 2 is a perspective view, similar to the view shown in FIG. 1, of the mapping probe in FIG. 1 which illustrates the electrode array assembly in a rolled-up configuration prior to insertion into the lumen of the catheter.

In order to fold the electrode array 5, the heating means is turned off. With the embodiment shown, the heating means has been arranged in two separate sections which are separated in the longitudinal direction of the catheter. FIG. 2 illustrates the state at which the back section of the heating means is turned off. As a result the back section of the carrier will cool down to body temperature and cause the carrier 18 to roll up along its longitudinal axis.

In order to complete the process and cause the carrier to move entirely into the folded state, the fluid which has been placed into the bag 19, is removed in order to produce the thickness of the electrode assembly 5.

Figure 3:
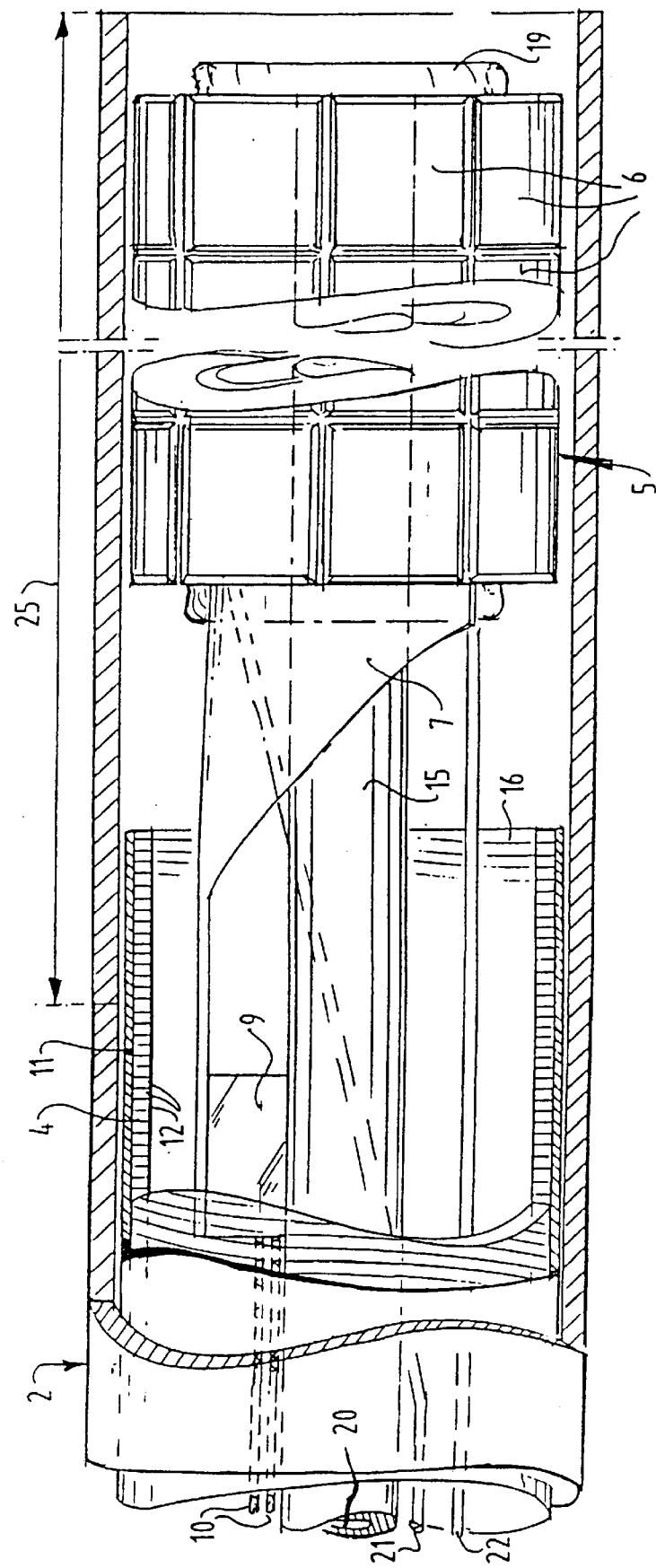
FIG. 3 is a sectional view, with portions broken away, which illustrates the electrode array assembly positioned within the lumen of the catheter.

After the first section of the carrier 18 has been folded, the second section of the heating means is turned off with the result that the front section of the carrier 18 will roll up in the direction of the arrows 24 to resume the folded state. Finally, the electrode array 5 can be pushed into the lumen of the outer catheter body 3 by pulling back on the inner tubing 4. Thus, the state as illustrated in FIG. 3 is brought about. In this state, the electrode assembly 5 has been moved inward over a distance 25, in the direction indicated by the arrow 23 of FIG. 2, so that the electrode array is enclosed completely by the outer catheter body 3.

As is apparent, with the introduction of the multielectrode catheter into the patient, the electrode array 5 is maintained in the folded and retracted position until the distal end of the catheter has reached the targeted position, in particular, the heart of the patient. When it is desired to expand the electrode array, the heating means is activated as a result of which the electrode array will unfold into the state illustrated in FIG. 1 and will be ready for use by the physician.

In another version of the multielectrode catheter as illustrated in FIG. 1, the support 15 may be constructed in a manner such that it can be retracted separately in relation to the inner tubing element 4. The support 15 will, in that case, be fixed to the carrier 18 only at the very distal section of the carrier 18. By moving the support 15, in relation to the inner tubing element 4, the carrier 18 and consequently the electrode array 5, will be deformed into a convex shape which provides an extra possibility to achieve proper contact with the electrode array with, for instance, the wall of the heart.

Referring now to FIG. 4, the catheter 30 comprises a pliable sheath such as a foil 33. The electrode array 34 has been arranged on the foil 33 for instance by use of deposition techniques. Along the two opposite sides, the sheath 33 is connected to the wire-like elements 35,36. The wire-like elements are received by an inner tube element 33 of the basic body 31 and extend, via an inner tube element 32 to the proximal end of the catheter. In addition to the two wires-like elements 35,36 along the edges of the sheath 33, a central wire-like element 37 has been arranged as well to support the sheath 33.

As may be seen in FIG. 5, the curve of the sheath 33 may be altered by rotating the wire-like elements 35,36 around a longitudinal axis. For this purpose these wire-like elements 35,36 have been provided with a control handle (not shown) at the proximal end from the basic body 31.

The inner tube element 32 is received by the basic body 31 in a movable manner, and by pulling on the proximal end of the tube element 33 the assembly of wire-like elements 35,36 and the foil connected thereto, can be pulled into the basic body 31. The wire-like elements 35,36 are resilient and are biased outwardly to automatically extend to stretch the foil 33.

The catheter illustrated in FIGS. 4 and 5 may also be further modified so that the sheath 33, and the electrode array 34, are arranged to curve around an axis at right angles to the longitudinal direction of the catheter. To achieve this result, the central wire-like element 37 will be constructed such that it can be moved separately from the inner tube element 32. By pulling on the wire-like element 37 at the proximal end of the catheter, the sheath 33 will curve, so that this element will curve in two directions along two axis at right angles to one another. Suitable manipulation of the elements 35, 36, 37 can consequently ensure proper contact between the electrode array 34 and the wall of the heart.

Figure 6:
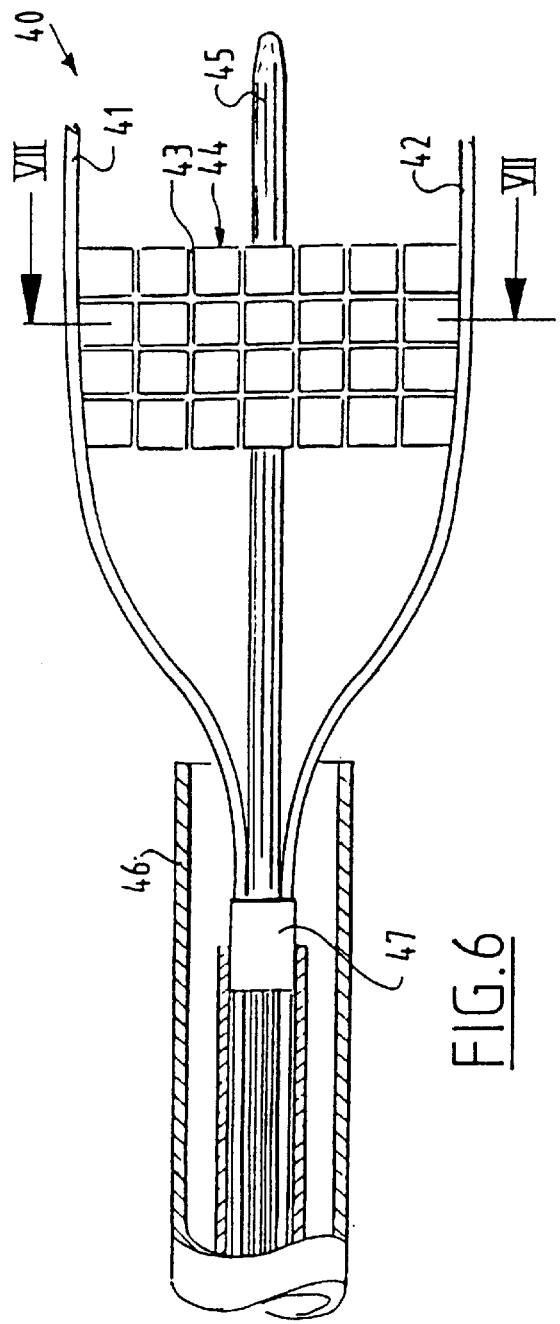
FIG. 6 is a perspective view, of still another embodiment of the present invention in which the electrode array assembly is wound-up on the inner tubing prior to insertion into the catheter.

As shown in FIG. 6, the catheter 40 comprises a catheter in the form of a foil 43 on top of which an electrode array 44 may be arranged. The foil 43 is connected with opposite sides to wire-like elements 41, 42, which are elastic and push the opposite sides of the sheath apart in a resilient manner, so that, in the unfolded state shown in FIG. 6, the carrier 43 is maintained in a stretched position. The sheath 43 is also connected to a central pin 45, which serves to support the sheath 43 and to fold the carrier in order to be able to retract it into the basic body 46.

Figure 7:
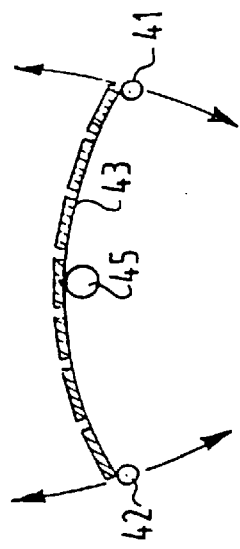
FIG. 7 shows a cross-sectional view, of FIG. 6 taken along the lines VII—VII of FIG. 6.

As may be seen in FIG. 7, a suitable curve may be imported to the sheath 43 carrying the electrode array 44, by rotating the wire-like elements 41, 42. The operative end of the catheter 40 has been received into the basic body 46 when inserting the catheter. As soon as the distal end of the catheter 40 has been placed at a position where the treatment is to be carried out, this operative end section is extended by moving the inner tube element 47 in a longitudinal direction in relation to the outer tube-like element 46.

Figure 8:
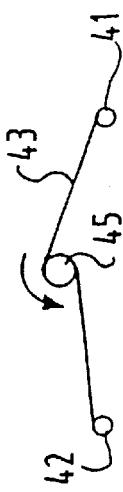
FIG. 8 illustrates the manner in which the electrode carrier of FIG. 5, 6 and 7 is wound prior to being inserted into the lumen of the catheter.

Following the treatment, the operative end is then drawn once again inside the basic body 46. To this end, the central pin 45 is turned in the direction shown in FIG. 8, as a result of which the sheath 43 is wound around the pin and the wire-like element 41,42. Thus, the assembly is gathered in to form a small diameter which may be received by the basic body 46 by pulling the inner tube element 47 in a proximal direction.

If during the mapping procedure an abnormal focus is found (one, for example, where the rate is more rapid than those foci found or proximal to the atrial focus and one which would govern the overall heart rate) it can be interrupted or destroyed by using a conductive path between any two of the electrodes to provide a more normal heart rate.

From the foregoing description, it will be apparent that the intravascular multielectrode cardiac mapping probe of the present invention has a number of advantages, some of which have been described above and others of which are inherent in the invention. Also, modifications may be made to the mapping probe without departing from the teachings of the present invention. Accordingly, the scope of the invention is only to be limited as necessitated by the accompanying claims.

We claim:

1. An intraventricular multielectrode cardiac mapping probe comprising:

a catheter having an open proximal end, an open distal end, and a lumen confluent with said open proximal end and said open distal end;

an elongate inner tubing slidably received and movable within said lumen of said catheter, said tubing having a distal end, a proximal end and a lumen extending through the length thereof; a plurality of elongate insulated conductor assemblies mounted within said lumen of said elongate inner tubing; and, an electrode array assembly including a flexible electrode carrier mounted on and carried by the distal end of the inner tubing and having a plurality of spaced-apart electrodes mounted on a face of said electrode carrier, each of said electrodes being in electrical continuity with one of said conductor assemblies, said electrode carrier being in a folded configuration and being positioned within the lumen of the catheter, the electrode carrier exhibits the characteristic that upon being released it returns to its original preformed generally planar configuration so that when the distal end of the catheter is placed in a desired position within the heart chamber the inner tubing may be slidably moved toward the distal end of the catheter to thereby cause the electrode array assembly to move out of the distal end of the catheter thereby causing the electrode array to expand from its retracted folded position within the lumen of the catheter to its preformed generally planar configuration outside of the catheter to thereby permit the measurement of electrical potentials at different points along the surface of the endocardial wall of the heart chamber;

wherein the electrode array assembly is comprised of a planar sheet of shape memory material in which the folded state occurs at less than about 45° centigrade and the unfolded generally planar state occurs at a temperature above about 45° centigrade.

2. A mapping probe as defined in claim 1, wherein the mapping probe includes heating means for heating the electrode array assembly to thereby cause the array to change from a folded state to an unfolded generally planar shape.

3. A mapping probe as defined in claim 2, wherein the shape memory material is comprised of nitinol.

4. An intraventricular multielectrode cardiac mapping probe comprising: a catheter having an open proximal end, an open distal end, and a lumen confluent with said open proximal end and said open distal end;

an elongate inner tubing slidably received and movable within said lumen of said catheter said tubing having a distal end, a proximal end and a lumen extending through the length thereof; a plurality of elongate insulated conductor assemblies mounted within said lumen of said elongate inner tubing; and an electrode array assembly including a flexible electrode carrier mounted on and carried by the distal end of the inner tubing and having a plurality of spaced-apart electrodes mounted on a face of said electrode carrier, each of said electrodes being in electrical continuity with one of said conductor assemblies, said electrode carrier being in a folded configuration and being positioned within the lumen of the catheter, the electrode carrier exhibits the characteristic that upon being released it returns to its original preformed generally planar configuration so that when the distal end of the catheter is placed in a desired position within the heart chamber the inner tubing may be slidably moved toward the distal end of the catheter to thereby cause the electrode array assembly to move out of the distal end of the catheter thereby causing the electrode array to expand from its retracted folded position within the lumen of the catheter to its preformed generally planar configuration outside of the catheter to thereby permit the measurement of electrical potentials at different points along the surface of the endocardial wall of the heart chamber;

wherein the electrode array assembly is rolled up along a longitudinal axis of the catheter in the folded configuration.

5. An intraventricular multielectrode cardiac mapping probe comprising: a catheter having an open proximal end, an open distal end, and a lumen confluent with said open proximal end and said open distal end;

an elongate inner tubing slidably received and movable within said lumen of said catheter, said tubing having a distal end, a proximal end and a lumen extending through the length thereof; a plurality of elongate insulated conductor assemblies mounted within said lumen of said elongate inner tubing; and an electrode array assembly including a flexible electrode carrier mounted on and carried by the distal end of the inner tubing and having a plurality of spaced-apart electrodes mounted on a face of said electrode carrier, each of said electrodes being in electrical continuity with one of said conductor assemblies, said electrode carrier being in a folded configuration and being positioned within the lumen of the catheter, the electrode carrier exhibits the characteristic that upon being released it returns to its original preformed generally planar configuration so that when the distal end of the catheter is placed in a desired position within the heart chamber the inner tubing may be slidably moved toward the distal end of the catheter to thereby cause the electrode array assembly to move out of the distal end of the catheter thereby causing the electrode array to expand from its retracted folded position within the lumen of the catheter to its preformed generally planar configuration outside of the catheter to thereby permit the measurement of electrical potentials at different points along the surface of the endocardial wall of the heart chamber;

wherein the electrode array assembly includes a resilient, compressible cushion interposed between the electrode carrier and the electrodes to thereby urge the electrodes against the interior wall of the heart when the electrode array assembly is in a performed generally planar configuration.

6. A mapping probe as defined in claim 5, wherein the resilient cushion takes the form of a flexible bag filled with a fluid.

7. An intraventricular multielectrode cardiac mapping probe comprising: a catheter having an open proximal end, an open distal end, and a lumen confluent with said open proximal end and said open distal end;

an elongate inner tubing slidably received and movable within said lumen of said catheter, said tubing having a distal end, a proximal end and a lumen extending through the length thereof; a plurality of elongate insulated conductor assemblies mounted within said lumen of said elongate inner tubing; and an electrode array assembly including a flexible electrode carrier mounted on and carried by the distal end of the inner tubing and having a plurality of spaced-apart electrodes mounted on a face of said electrode carrier, each of said electrodes being in electrical continuity with one of said conductor assemblies, said electrode carrier being in a folded configuration and being positioned within the lumen of the catheter the electrode carrier exhibits the characteristic that upon being released it returns to its original preformed generally planar configuration so that when the distal end of the catheter is placed in a desired position within the heart chamber the inner tubing may be slidably moved toward the distal end of the catheter to thereby cause the electrode array assembly to move out of the distal end of the catheter thereby causing the electrode array to expand from its retracted folded position within the lumen of the catheter to its preformed generally planar configuration outside of the catheter to thereby permit the measurement of electrical potentials at different points along the surface of the endocardial wall of the heart chamber;

wherein the electrode array assembly includes at least two wires with a sheet of foil extending between said wires and the spaced-apart electrodes being mounted on the sheet of foil.

8. A mapping probe as defined in claim 7, wherein the electrode array assembly also includes rotatable pins which are positioned along a central axis and equally spaced between the wires and being attached to the central section of the sheet of foil so that upon rotation of the pin the foil is caused to roll up on the pin thereby causing the wires to be retracted from preformed expanded positions to positions proximate the rotating pin.

* * * * *